(12) United States Patent
Makovec et al.

(10) Patent No.: US 7,906,501 B2
(45) Date of Patent: Mar. 15, 2011

(54) PYRROLE DERIVATIVES WITH ANGIOTENSIN II ANTAGONIST ACTIVITY

(75) Inventors: Francesco Makovec, Lesmo (IT); Roberto Artusi, Rho (IT); Antonio Giordani, Pavia (IT); Simona Zanzola, Milan (IT); Lucio Claudio Rovati, Monza (IT)

(73) Assignee: Rottapharm S.p.A., Milan (IT)

( * ) Notice: Subject to any disclaimer, the term of this patent is extended or adjusted under 35 U.S.C. 154(b) by 189 days.

(21) Appl. No.: 11/568,362

(22) PCT Filed: Apr. 27, 2005

(86) PCT No.: PCT/EP2005/051911
§ 371 (c)(1), (2), (4) Date: Oct. 26, 2006

(87) PCT Pub. No.: WO2005/105789
PCT Pub. Date: Nov. 10, 2005

(65) Prior Publication Data
US 2007/0244170 A1 Oct. 18, 2007

(30) Foreign Application Priority Data
Apr. 28, 2004 (IT) .................................. TO04A0264

(51) Int. Cl.
*A61K 31/41* (2006.01)
*C07D 293/00* (2006.01)
*C07D 257/04* (2006.01)
*C07D 403/10* (2006.01)
*C07D 295/04* (2006.01)

(52) U.S. Cl. ......... 514/183; 514/381; 514/422; 514/427; 548/100; 548/250; 548/400; 548/518; 548/564; 548/578

(58) Field of Classification Search .................. 548/250, 548/564
See application file for complete search history.

(56) References Cited

FOREIGN PATENT DOCUMENTS

| EP | 0253310 | 1/1988 |
| EP | 0323841 | 7/1989 |

OTHER PUBLICATIONS

Carini et al., J. Med. Chem. 1991, vol. 34 (8), pp. 2525-2547.*
Prasun K Charravarty, Antihypertensive Agents, Expert Opinion on Therapeutic Patents, Ashley Publications, GB, vol. 5, No. 5, May 1, 1995, pp. 431-458, XP00567227.
Ruth R. Wexler, Nonpeptide Angiotensin II Receptor Antagonists: The Next Generation in Antihypertensive Therapy, Journal of Medicinal Chemistry, vol. 39, No. 3, Feb. 2, 1996.
David J. Dzielak, Comparative pharmacology of the angiotensin II receptor antagonists, Ashley Publications Let., ISSN 1354-3784, 1998.
F. Haber, Berichte Der Deutschen Chemischen Gesellschaft, Verlag Chemie, G.M.B.H., Berlin, 1927.
Kiitiro Utimoto, Palladium-Catalyzed Synthesis of Pyrroles, Tetrahedron Letters, vol. 223, No. 43, pp. 4277-4278, 1981, Pergamon Press Ltd.
Robert A. Benkeser, The Stereochemistry of the Addition of Silicochloroform to Acetylenes, Contribution from the Chemical Laboratories of Purdue University, Mar. 19, 1958, vol. 80, pp. 5298-5300.
Huang-Minlon, A Simple Modification of the Wolff-Kishner Reduction, Contribution from the Chemical Laboratories of Harvard University, Dec. 1946, vol. 68, pp. 2487-2488.
Philip E. Sonnet, Synthesis of Beta-Substituted Pyrroles via 1-(Pyrrol-2-ylmethylene)pyrrolidinium Salts, Entomology Research Division, Agricultural Research Service, U.S. Department of Agriculture, Sep. 2, 1970, J. Org. Chem, vol. 36, No. 7, 1971, pp. 1005-1007.
R.S. L. Chang, In Vitro Pharmacology of L-158, 809, a New Highly Potent and Selective Angiotensin II Receptor Antagonist, The Journal of Pharmacology and Experimental Therapuetics, 1992, vol. 262, No. 1, pp. 133-138.
M. J. Robertson, Pharmacological profile of GR117289 in vitro: a novel, potent and specific non-peptide angiotensin AT1 receptor antagonist, Br. J. Pharmacol. (1992), 107, 1173-1180, Macmillan Press Ltd.
Marie-Catherine GRES, Correlation Between Oral Drug Absorption in Humans, and Apparent Drug Permeability in TC-7 Cells, A Human Epithelial Intestinal Cell Line: Comparison with the Parental Caco-2 Cell Line, Parmaceutical Research, vol. 15, No. 5, 1998, pp. 726-733.

* cited by examiner

*Primary Examiner* — Ardin Marschel
*Assistant Examiner* — Gregg Polansky
(74) *Attorney, Agent, or Firm* — Roylance, Abrams, Berdo & Goodman, L.L.P.

(57) ABSTRACT

Compounds which may be represented by the general formula (I) shown below and in which: $R_1$ is a group independently selected from among: CHO, —COOH, —$CH_2OH$ $R_2$ is hydrogen or a linear or branched $C_1$-$C_6$ alkyl group $R_3$ is hydrogen or a halogen group selected from among Cl and Br $R_4$ is a linear or branched $C_3$-$C_5$ alkyl group and the pharmaceutically acceptable salts thereof such as the sodium or potassium salt. The compounds exhibit potent and selective AII antagonist activity and are useful for the treatment of any disorders in which elevated synthesis of AII or overexpression of the $AT_1$ receptor may play a primary pathological role, as in the case of arterial hypertension, congestive cardiac insufficiency, platelet aggregation and disorders associated therewith such as for example myocardial and cerebral infarction, renal ischaemia, venous and arterial thrombosis, peripheral vasculopathy, pulmonary hypertension, diabetes mellitus, diabetic neuropathy, glaucoma and diabetic retinopathy.

(I)

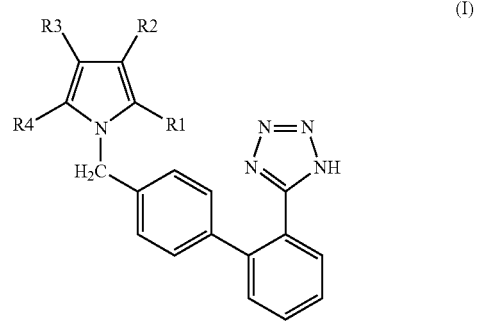

6 Claims, No Drawings

PYRROLE DERIVATIVES WITH ANGIOTENSIN II ANTAGONIST ACTIVITY

The present invention provides novel pyrrole derivatives which may be represented by the general formula (I) shown below and in which:

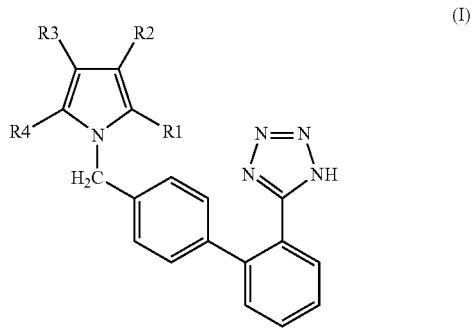

$R_1$ is a group independently selected from among:
—CHO, —COOH, —CH$_2$OH; $R_2$ is hydrogen or a linear or branched $C_1$-$C_6$ alkyl group; $R_3$ is hydrogen or a halogen group selected from among Cl and Br; $R_4$ is a linear or branched $C_3$-$C_5$ alkyl group and the pharmaceutically acceptable salts thereof such as for example the sodium or potassium salt.

The compounds of the present invention are proving to be potent angiotensin II (AII) receptor antagonists by interacting with the specific $AT_1$ type receptors thereof on the surface of target cells. $AT_1$ receptors, which play a central part in controlling arterial blood pressure, have mainly been identified in the adrenal cortex, in the kidneys and more recently also on the surface of platelets. Binding of AII with the $AT_1$ receptor brings about vasoconstriction, an increase in aldosterone secretion, an increase in platelet aggregation and in arterial pressure. AII is thus considered to be one of the principal aetiological factors in bringing about arterial hypertension and cardiovascular disorders.

Given the significance of AII in controlling arterial pressure and kidney function, very many different classes of non-peptide AII receptor inhibitors have been synthesised to date. The prototype for these $AT_1$ antagonists is losartan, an imidazole derivative characterised by the presence of the biphenyl tetrazole group (BPT) group in its chemical structure. This drug is used for the treatment of arterial hypertension. Other compounds, generally heterocyclic derivatives, such as eprosartan, candesartan, telmisartan and valsartan have subsequently entered into therapeutic use. The latter compound is an amino acid derivative while still comprising the group BPT in its structure. In addition to those mentioned above, many other $AT_1$ antagonists have been subjected to preclinical and subsequently human pharmacological trials [see for example the monographs: "Antihypertensive agents; P. K. Chakravarty, Exp. Opin. Ther. Patents (1996) 5 (5): 431-458 (Ashley Pub.)"; "Nonpeptide Angiotensin II Receptor Antagonists; The Next Generation Antihypertensive Therapy; R. R. Wexler et al., J. Med. Chem. (1996) 39 (3): 625-656; "Comparative pharmacology of the angiotensin II receptor antagonists; D. J. Dzielak, Exp. Opin. Invest. Drugs (1998) 7 (5): 741-751. (Ashley Pub.)"].

Of the other heterocyclic structures used to synthesise $AT_1$ antagonist compounds, pyrrole, as described for the compounds provided by the present invention, had already been used by others. However, the derivatives synthesised by Carini et al. [European patent EP 0 323 841 (1993)] differed substantially from those described herein and, as will be demonstrated further below, exhibited levels of activity which were hardly worthwhile.

The object of the present invention is to provide novel drugs for therapeutic use which exhibit potent and selective AII antagonist activity for the treatment of any disorders in which elevated synthesis of AII or overexpression of the $AT_1$ receptor may play a primary pathological role, as in the case of arterial hypertension, congestive cardiac insufficiency, platelet aggregation and disorders associated therewith such as for example myocardial and cerebral infarction, renal ischaemia, venous and arterial thrombosis, peripheral vasculopathy, pulmonary hypertension, diabetes mellitus, diabetic neuropathy, glaucoma and diabetic retinopathy.

Dosage forms of the compounds provided by the invention may be prepared according to conventional methods such as for example tablets, capsules, suspensions, solutions, patches and may be administered orally, parenterally, transdermally, transmucosally, ocularly or other appropriate manner to achieve the therapeutic effect, such as for example solid preparations for oral use with extended action which permit controlled release of the active substance over time.

The active ingredient is usually administered to the patient in a reference dose which may range from 0.125 to 5 mg/kg body weight per dose. For administration by parenteral and ocular routes, it is preferable to use a water-soluble salt of the compounds provided, such as the sodium or potassium salt or another non-toxic and pharmaceutically acceptable salt.

Inactive ingredients which may be used are substances commonly used in pharmaceutical technology as excipients, binders, flavourings, disintegrants, transdermal and transmucosal absorption promoters, colorants, humectants etc. and, in the case of ocular administration, pharmaceutically acceptable preservatives may also be used.

The process for the preparation of the derivatives provided by the invention consists of a series of reactions which comprises:
a) preparing the pyrrole derivatives 1e (see scheme 1) which consists in reacting a suitable $R_4$ trimethylsilylalkyne, in which $R_4$ has the above-stated meaning, with an $R_2$ acyl chloride in which $R_2$ has the above-stated meaning, in the presence of $AlCl_3$ (step 1) to yield the corresponding ketoalkyne 1a, which, by treatment with trimethylsilylcyanide under a nitrogen atmosphere, yields the corresponding CN addition derivative 1b (step 2), which, by reduction with $LiAlH_4$, yields the corresponding amine 1c (step 3) and which, by subsequent treatment with $PdCl_2$ and refluxing in an inert solvent such as acetonitrile, yields the corresponding pyrrole derivative 1d (step 4), which is finally subjected to Vilsmeier formylation [Ber. (1927), 60, 119] to yield the corresponding, appropriately substituted 2-pyrrolaldehyde 1e (step 5).

Scheme 1

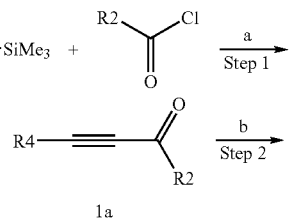

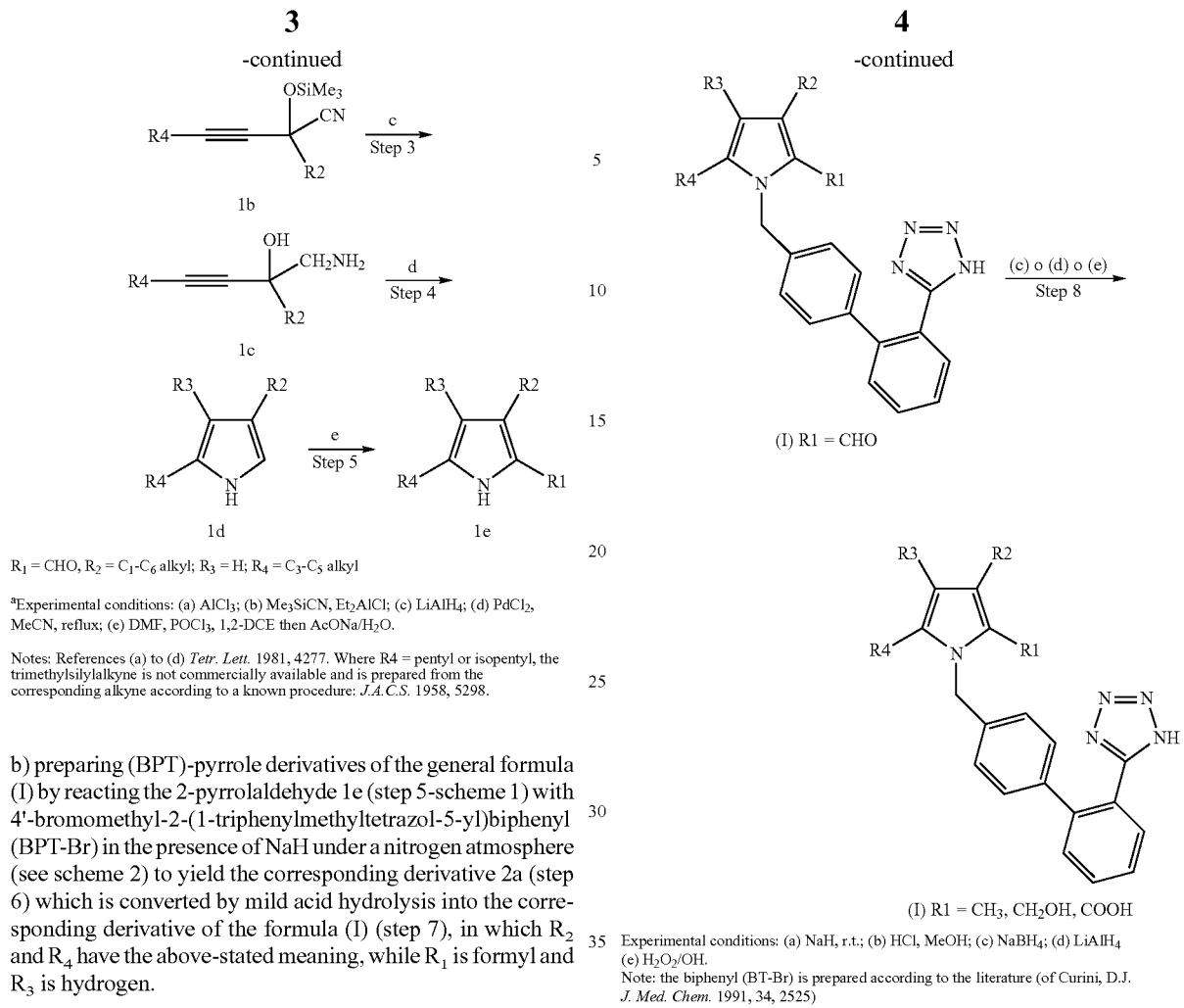

$R_1$ = CHO, $R_2$ = $C_1$-$C_6$ alkyl; $R_3$ = H; $R_4$ = $C_3$-$C_5$ alkyl

[a]Experimental conditions: (a) AlCl$_3$; (b) Me$_3$SiCN, Et$_2$AlCl; (c) LiAlH$_4$; (d) PdCl$_2$, MeCN, reflux; (e) DMF, POCl$_3$, 1,2-DCE then AcONa/H$_2$O.

Notes: References (a) to (d) Tetr. Lett. 1981, 4277. Where R4 = pentyl or isopentyl, the trimethylsilylalkyne is not commercially available and is prepared from the corresponding alkyne according to a known procedure: J.A.C.S. 1958, 5298.

b) preparing (BPT)-pyrrole derivatives of the general formula (I) by reacting the 2-pyrrolaldehyde 1e (step 5-scheme 1) with 4'-bromomethyl-2-(1-triphenylmethyltetrazol-5-yl)biphenyl (BPT-Br) in the presence of NaH under a nitrogen atmosphere (see scheme 2) to yield the corresponding derivative 2a (step 6) which is converted by mild acid hydrolysis into the corresponding derivative of the formula (I) (step 7), in which $R_2$ and $R_4$ have the above-stated meaning, while $R_1$ is formyl and $R_3$ is hydrogen.

Scheme 2

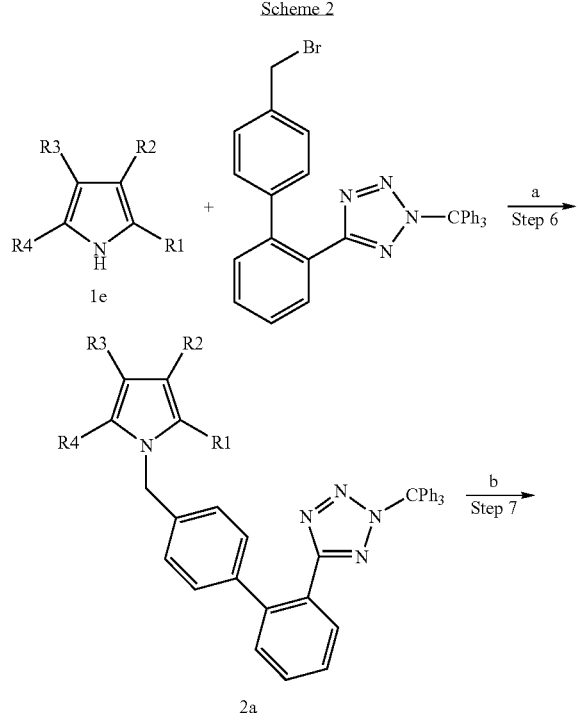

(I) R1 = CHO (I) R1 = CH$_3$, CH$_2$OH, COOH

Experimental conditions: (a) NaH, r.t.; (b) HCl, MeOH; (c) NaBH$_4$; (d) LiAlH$_4$ (e) H$_2$O$_2$/OH.
Note: the biphenyl (BT-Br) is prepared according to the literature (of Curini, D.J. J. Med. Chem. 1991, 34, 2525)

The 2-formyl pyrrole derivatives of the general formula (I) obtained in this manner may be converted into the corresponding carboxylic acids or alcohols by treatment respectively with H$_2$O$_2$ or by reduction with NaBH$_4$ in methanol under refluxing conditions (step 8, scheme 2). For comparison purposes, the corresponding methyl derivative ($R_1$=CH$_3$) was also synthesised by reduction with LiAlH$_4$ (step 8, scheme 2).

The 2-formyl pyrrole derivatives of the general formula (I), in which $R_1$ is CHO, $R_2$ is H, $R_3$ is H, Br or CL, $R_4$ is $C_3$-$C_5$ alkyl are prepared (see scheme 3) by reacting pyrrole with the appropriate N,N-dimethylacylamide (DMP) in the presence of POCl$_3$ and subsequent hydrolysis with sodium acetate to yield the corresponding 2-acylpyrrole which, by subsequent reduction with hydrazine and potash [according to Huang-Minlon; J.A.C.S. 1946, 68, 2487], is converted into the corresponding 2-alkylpyrrole 3a (step 1, 2) which is formylated as seen above in scheme 1 to yield the corresponding formyl derivative 3b (step 3) which, by subsequent treatment with N-bromosuccinimide (NBS), yields the corresponding bromo derivative 3c (step 4d) or, by treatment with pyrrolidine and HClO$_4$ and subsequent chlorination with sulfuryl chloride [Sonnet P. E. J.O.C. 1971, 36, 1005], yields the corresponding chloro derivative 3c (step 4e, f).

Scheme 3

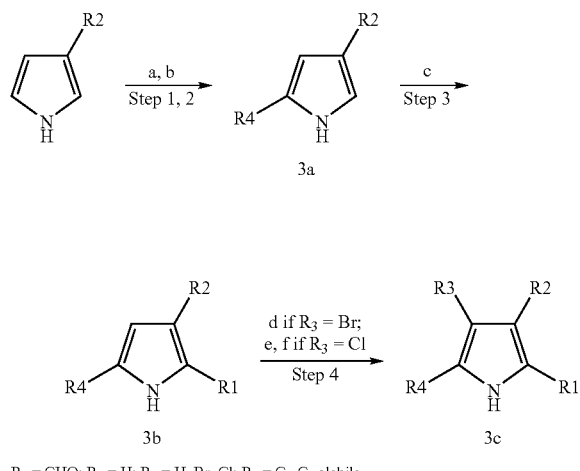

$R_1$ = CHO; $R_2$ = H; $R_3$ = H, Br, Cl; $R_4$ = $C_3$-$C_5$ alchile

Experimental conditions: (a) POCl$_3$, DMP, AcONa; (b) N$_2$H$_4$, KOH; (c) POCl$_3$, DMF, AcONa, (d) NBS; (e) pyrrolidine; (f) SO$_2$Cl$_2$.

The formyl derivatives 3c are finally converted into the final compounds of the formula (I) by means of treatment with 4'-bromomethyl-2-(1-triphenylmethyltetrazol-5-yl) biphenyl in the presence of NaH as described in scheme 2 (step 7). For comparison purposes, the compound 2,5-dimethyl-1-[2'(1H-tetrazol-5-yl)biphenyl-4-yl-methyl]pyrrole (compound 14) was also synthesised as shown in the following scheme (scheme 4):

Scheme 4-Preparation of compound 14

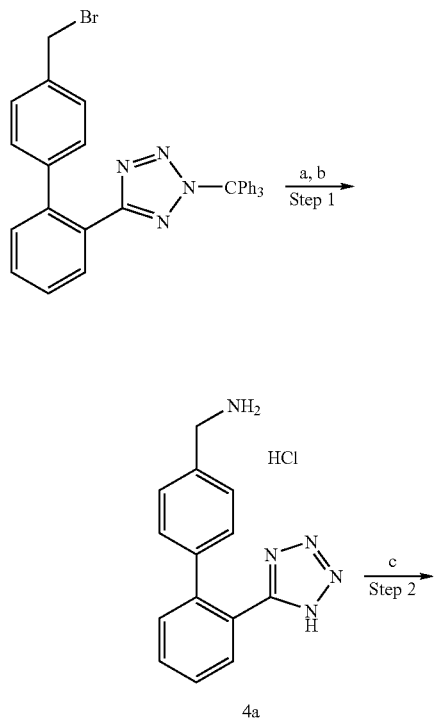

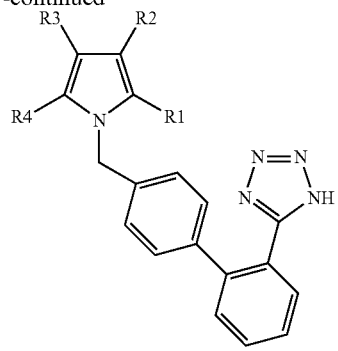

(I) $R_1$ = $R_4$ = CH$_3$; $R_2$ = $R_3$ = H

Experimental conditions: (a) CF$_3$CONH$_2$, t-BuOK; (b) KOH(aq) then HCl 4N; (c) acetonylacetone, AcOH, reflux.

The following Examples are given below to illustrate the invention in greater detail.

EXAMPLE 1

Preparation of 5-n-butyl-1-[2-(1H-tetrazol-5-yl)biphenyl-4-yl-methyl]-3-[3-(2-methyl)propyl]-2-pyrrolaldehyde (1) (compound 1 of Table 1)

Scheme 1

Step 1. 2-Methyl-5-decyn-4-one (1a)

21.6 g of AlCl$_3$ (0.162 moles) in 65 mL of CCl$_4$ are cooled to 2° C. and 19.7 mL of isovaleroyl chloride (0.162 moles) in 30 mL of CCl$_4$ are added dropwise. 25 g of trimethylsilylhexyne (0.162 moles) in 30 mL of CCl$_4$ are then added dropwise. The mixture is stirred for 1 h at 2° C. and for 24 h at ambient temperature. It is poured into 200 mL of 1:3 37% HCl/ice, stirred for 1 h, the phases are separated and the aqueous phase is extracted with CH$_2$Cl$_2$. The combined organic phases are washed to neutrality, dried with Na$_2$SO$_4$ and evaporated. 27 g of product are obtained, which are used in the subsequent step without further purification. Formula: C$_{11}$H$_{18}$O (m.w. 166.27). Quantitative yield. IR (film) 2956; 2209; 1670 cm$^{-1}$.

Step 2.
4-Cyano-2-methyl-4-trimethylsilyloxy-5-decyne (1b)

27 g of (1a) (0.162 moles) and 23.8 mL of trimethylsilylcyanide (0.178 moles) are mixed under a nitrogen atmosphere. 1.8 mL of Et$_2$AlCl (25% soln. in toluene, 3.24 mmol) are added dropwise and the mixture is stirred for 6 h. The excess trimethylsilylcyanide is evaporated. 43 g of product are obtained, which are used in the subsequent step without further purification. Formula: C$_{15}$H$_{27}$NOSi (m.w. 265.47). Quantitative yield. IR (film) 2959; 2237; 1610 cm$^{-1}$.

Step 3. 2-iso-Butyl-2-hydroxy-3-octyn-1-ylamine (1c)

Under a nitrogen atmosphere, 6.3 g of LiAlH$_4$ (0.167 moles) are suspended in 250 mL of anhydrous diethyl ether and the temperature is reduced to 0° C. 43 g of (1b) (0.162 moles) in 75 mL of anhydrous diethyl ether are added dropwise and the mixture is stirred for 20 h. LiAlH$_4$ is hydrolysed with water and 30% NaOH and the phases are separated. The aqueous phase is extracted repeatedly with diethyl ether, the organic phase is extracted with 1N HCl, the aqueous phase is alkalised with 30% NaOH, extracted with diethyl ether, the combined organic phases are washed to neutrality, dried with $Na_2SO_4$ and evaporated. 20.8 g of product are obtained, which are used in the subsequent step without further purification. Formula: $C_{12}H_{23}NO$ (m.w. 197.32). Yield 65%.

Step 4. 4-n-Butyl-3-[3-(2-methyl)propyl]pyrrole (1d)

Under a nitrogen atmosphere, 20.8 g of (1c) (0.105 moles) are dissolved in 300 mL of acetonitrile, 186 mg of $PdCl_2$ (1.05 mmol) are added and the mixture is heated to reflux for 15 h. The solvent is evaporated and the crude product is purified by means of flash chromatography using 4:1 hexane/ethyl acetate as the eluent mixture. 8.3 g of product are obtained, which are used in the subsequent step. Formula: $C_{12}H_{21}N$ (m.w. 179.30). Yield 44%. IR (film) 3381; 2926; 1660 $cm^{-1}$.

Step 5. 4-n-Butyl-3-[3-(2-methyl)propyl]-2-pyrrolaldehyde (1e)

3.9 mL of DMF (0.051 moles) are cooled to 0-5° C. and 4.7 mL of $POCl_3$ (0.051 moles) are slowly added dropwise. The mixture is stirred at ambient temperature for 15 minutes, then diluted with 27 mL of 1,2-dichloroethane (1,2-DCE) and cooled to 0° C. 8.3 g of (1d) (0.046 moles) in 40 mL of 1,2-DCE are added dropwise and the mixture is heated to reflux for 30 minutes. The mixture is allowed to cool and is diluted with a solution of sodium acetate (21.3 g, 0.259 moles) in 42 mL of water and is then heated to reflux for a further 30 minutes. The phases are separated, the aqueous phase is extracted with $CH_2Cl_2$, the combined organic phases are washed to neutrality, dried with $Na_2SO_4$ and evaporated. The crude product is purified by means of flash chromatography using 4:1 hexane/ethyl acetate as the eluent mixture. 7.2 g of product are obtained, which are used in the subsequent step. Formula: $C_{13}H_{21}NO$ (m.w. 207.29). Yield 76%. IR (film) 3252; 2955; 1631 $cm^{-1}$.

Scheme 2

Step 6. 5-n-Butyl-1-[2'-(1-triphenylmethyltetrazol-5-yl)biphenyl-4-yl-methyl]-3-[3-(2-methyl)propyl]-2-pyrrolaldehyde (2a)

Under a nitrogen atmosphere, 1.7 g of NaH (0.043 moles) are suspended in 250 mL of anhydrous dimethylformamide (DMF) and 7.2 g of pyrrolaldehyde (0.036 moles) are added in portions. After 3 h, 21.9 g of 4'-bromomethyl-2-(1-triphenylmethyltetrazol-5-yl)biphenyl (0.036 moles) are added in portions and the mixture is left to stand at ambient temperature for 48 h. The mixture is poured into water, extracted with diethyl ether, the combined organic phases are washed with water, dried with $Na_2SO_4$ and evaporated. The crude product is purified by means of flash chromatography using 4:1 hexane/ethyl acetate as the eluent mixture. 20.5 g of product are obtained, which are used in the subsequent step. Formula: $C_{46}H_{45}N_5O$ (m.w. 687.09). Yield 83%.

Step 7. 5-n-Butyl-1-[2'-(1H-tetrazol-5-yl)biphenyl-4-yl-methyl]-3-[3-(2-methyl)propyl]-2-pyrrolaldehyde (compound 1)

20.5 g of compound 2a (0.030 moles) are dissolved in 510 mL of 1:50 THF/MeOH, the mixture is cooled to 0° C. and 37.5 mL of 4N HCl in water (0.150 moles) are added dropwise. The mixture is left to stand at 0° C. for 1 h and at ambient temperature for 2 h. The mixture is neutralised with a saturated solution of $NaHCO_3$ and the solvent is evaporated. The mixture is acidified to pH 4 with citric acid and the product is filtered out and washed to neutrality with water. Drying is performed in a vacuum oven at 50° C. Product: 6.6 g. Formula: $C_{27}H_{31}N_5O$ (m.w. 441.58). Yield 50%.

Prepared in a similar manner (c.f. Table 1):
5-n-Propyl-3-isopropyl-1-[2'-(1H-tetrazol-5-yl)biphenyl-4-yl-methyl]-2-pyrrolaldehyde (compound 5).
5-n-Butyl-3-isopropyl-1-[2'-(1H-tetrazol-5-yl)biphenyl-4-yl-methyl]-2-pyrrolaldehyde (compound 6).
5-n-Pentyl-3-isopropyl-1-[2'-(1H-tetrazol-5-yl)biphenyl-4-yl-methyl]-2-pyrrolaldehyde (compound 8).
5-[(3-Methyl)butyl]-3-isopropyl-1-[2'-(1H-tetrazol-5-yl)biphenyl-4-yl-methyl]-2-pyrrolaldehyde (compound 9).

The same method may be used to prepare the compounds 5-n-butyl-1-[2'-(1H-tetrazol-5-yl)biphenyl-4-yl-methyl]-3-[3-(2,2-dimethyl)propyl]-2-pyrrolaldehyde and 5-n-butyl-1-[2'-(1H-tetrazol-5-yl)biphenyl-4-yl-methyl]-3-[4-(2-methyl)butyl]-2-pyrrolaldehyde.

EXAMPLE 2

Scheme 3

Step 1. 2-n-Propionylpyrrole 100 mL of N,N-dimethylpropionamide (0.909 moles) are cooled to 0-5° C. and 83.4 mL of $POCl_3$ (0.909 moles) are slowly added dropwise. The mixture is stirred at ambient temperature for 15 minutes, then diluted with 200 mL of 1,2-dichloroethane (1,2-DCE) and cooled to 0° C. 57.4 mL of pyrrole (0.827 moles) in 100 mL of 1,2-DCE are added dropwise and the mixture is heated to reflux for 30 minutes. The mixture is allowed to cool and is diluted with a solution of sodium acetate (380 g, 4.63 moles) in 800 mL of water and is then heated to reflux for a further 30 minutes. The phases are separated, the aqueous phase is extracted with $CH_2Cl_2$, the combined organic phases are washed to neutrality, dried with $Na_2SO_4$ and evaporated. The crude product is purified by means of vacuum distillation (3.5 mbar, 110-117° C.). 100 g of product are obtained, which are used in the subsequent step. Formula: $C_7H_9NO$ (m.w. 123.15). Yield 98%.

Step 2. 2-n-Propylpyrrole (3a)

116 g of KOH (2.07 moles) are suspended in 700 mL of diethylene glycol and 75 g of 2-propionylpyrrole (0.609 moles) and 86 mL of hydrazine hydrate (1.77 moles) are added. The mixture is heated to reflux in a Dean-Stark apparatus. The phases are separated, the upper phase is washed with water, dried with $Na_2SO_4$ and evaporated. 40 g of product are obtained, which are used in the subsequent step without further purification. Formula: $C_7H_{11}N$ (m.w. 109.17). Yield 60%.

Step 3. 5-n-Propyl-2-pyrrolaldehyde (3b)

This compound was prepared using the same procedure as in Example 1, scheme 1, step 5.4 g of (2a) (0.036 moles), 3.7 mL of $POCl_3$ (0.040 moles) and 3.1 mL of DMF (0.040 moles) yield 3.9 g of product which are used in the subsequent step. Formula: $C_8H_{11}NO$ (m.w. 125.00). Yield 78%.

Scheme 2

Step 6. 5-n-Propyl-1-[2'-(1-triphenylmethyltetrazol-5-yl)biphenyl-4-yl-methyl]-2-pyrrolaldehyde (2a)

This compound was prepared using the same procedure as in Example 1. 3.9 g of 5-n-propyl-2-pyrrolaldehyde (0.031 moles) and 15 g of 4'-bromomethyl-2-(1-triphenylmethyltetrazol-5-yl)-biphenyl (0.031 moles) yield 15 g of product which are used in the subsequent step. Formula: $C_{41}H_{35}N_5O$ (m.w. 613.76). Yield 78%.

Step 7. 5-n-Propyl-1-[2'-(1H-tetrazol-5-yl)biphenyl-4-yl-methyl]-2-pyrrolaldehyde (compound 2)

This compound was prepared using the same procedure as in Example 1.15 g of 5-n-propyl-1-[2'-(1-triphenylmethyltetrazol-5-yl)biphenyl-4-yl-methyl]-2-pyrrolaldehyde (0.024 moles) and 30 mL of 4N HCl (0.120 moles) yield 6.3 g of product. Formula: $C_{22}H_{21}N_5O$ (m.w. 371.44). Yield 71%.

Prepared in a similar manner (c.f. Table 1):
5-n-Butyl-1-[2'-(1H-tetrazol-5-yl)biphenyl-4-yl-methyl]-2-pyrrolaldehyde (compound 7).

EXAMPLE 3

Scheme 3

Step 4. 4-Bromo-5-n-propyl-2-pyrrolaldehyde 15 g of 5-n-propyl-2-pyrrolaldehyde (0.11 moles) are dissolved in 600 mL of $CCl_4$ under a nitrogen atmosphere. 23 g of NBS (0.13 moles) are added and the mixture is heated to 50° C. for 6 h. The succinimide is filtered out, the organic phase is washed with a saturated solution of $NaHCO_3$, dried with $Na_2SO_4$ and evaporated. 14 g of product are obtained, which are used in the subsequent step. Formula: $C_8H_{10}BrNO$ (m.w. 216.08). Yield 60%.

Scheme 2

Step 6. 4-Bromo-5-n-propyl-1-[2'-(1-triphenylmethyltetrazol-5-yl)biphenyl-4-yl-methyl]-2-pyrrolaldehyde (2a)

This compound was prepared using the same procedure as in Example 1. 4.3 g of 4-bromo-5-n-propyl-2-pyrrolaldehyde (0.020 moles) and 11 g of 4'-bromomethyl-2-(1-triphenylmethyltetrazol-5-yl)biphenyl (0.020 moles) yield 10 g of product which are used in the subsequent step. Formula: $C_{41}H_{34}BrN_5O$ (m.w. 692.66). Yield 75%.

Step 7. 4-Bromo-5-n-propyl-1-[2'-(1H-tetrazol-5-yl)biphenyl-4-yl-methyl]-2-pyrrolaldehyde (compound 3)

This compound was prepared using the same procedure as in Example 1.10 g of 4-bromo-5-n-propyl-1-[2'-(1-triphenylmethyltetrazol-5-yl)biphenyl-4-yl-methyl]-2-pyrrolaldehyde (0.015 moles) and 19 mL of 4N HCl (0.075 moles) yield 3.5 g of product. Formula: $C_{22}H_{20}BrN_5O$ (m.w. 450.34). Yield 52%.

EXAMPLE 4

Scheme 3

Step 4. 4-Chloro-5-n-propyl-2-pyrrolaldehyde 3.25 g of pyrrolidine (0.039 moles) and 5.51 g of $HClO_4$ 70% are heated to reflux in 28 mL of 1:1 benzene/ethyl acetate in a Dean-Stark apparatus until the water has been completely removed (approx. 3 h). 5.4 g of 5-n-propyl-2-pyrrolaldehyde (0.039 moles) are added and the mixture is again heated to reflux in a Dean-Stark apparatus (1 h). The solvent is evaporated and the 11 g of oil obtained (0.039 moles) are used, being dissolved in 80 mL of 1,2-DCE and the mixture cooled to 5° C. 5.2 g of sulfuryl chloride (0.039 moles) dissolved in 10 mL of 1,2-DCE are slowly added dropwise and the mixture is left to stand at 5° C. for 1 h and at ambient temperature for 24 h. The solvent is evaporated and the residue is redissolved with diethyl ether. Washing is performed repeatedly with a saturated solution of $NaHCO_3$, with 1N HCl, water, the mixture is dried with $Na_2SO_4$ and evaporated. 5.2 g of product are obtained, which are used in the subsequent step without further purification. Formula: $C_8H_{10}ClNO$ (m.w. 171.62). Yield 78%.

Scheme 2

Step 6. 4-Chloro-5-n-propyl-1-[2'-(1-triphenylmethyltetrazol-5-yl)biphenyl-4-yl-methyl]-2-pyrrolaldehyde (2a)

This compound was prepared using the same procedure as in Example 1. 5.2 g of 4-chloro-5-n-propyl-2-pyrrolaldehyde (0.030 moles) and 16.9 g of 4'-bromomethyl-2-(1-triphenylmethyltetrazol-5-yl)biphenyl (0.030 moles) yield 12 g of product which are used in the subsequent step. Formula: $C_{41}H_{34}ClN_5O$ (m.w. 648.21). Yield 60%.

Step 7. 4-Chloro-5-n-propyl-1-[2'-(1H-tetrazol-5-yl)biphenyl-4-yl-methyl]-2-pyrrolaldehyde (compound 4)

This compound was prepared using the same procedure as in Example 1.12 g of 4-chloro-5-n-propyl-1-[2'-(1-triphenylmethyltetrazol-5-yl)biphenyl-4-yl-methyl]-2-pyrrolaldehyde (0.019 moles) and 24 mL of 4N HCl (0.095 moles) yield 5.0 g of product. Formula: $C_{22}H_{20}ClN_5O$ (m.w. 405.89). Yield 65%.

EXAMPLE 5

Scheme 2

Step 8. 5-n-Propyl-1-[2'-(1H-tetrazol-5-yl)biphenyl-4-yl-methyl]-2-pyrrolecarboxylic acid (compound 10)

100 mg of compound 2 (0.269 mmol) are dissolved in 50 mL of 0.1 N NaOH and 158 mL (1.6 mmol) of 35% $H_2O_2$ are added. The mixture is left to stand at ambient temperature for 18 h. The mixture is cooled to 0° C. and adjusted to pH 2 with 2N HCl. The solid is filtered out and washed with water. Drying is performed in a vacuum oven at 40° C. Product: 54 mg. Formula: $C_{22}H_{21}N_5O_2$ (m.w. 387.43). Yield 52%.

Prepared in a similar manner (c.f. Table 1):
5-n-Propyl-3-isopropyl-1-[2'-(1H-tetrazol-5-yl)biphenyl-4-yl-methyl]-2-pyrrolecarboxylic acid (compound 11).
5-n-Butyl-1-[2'-(1H-tetrazol-5-yl)biphenyl-4-yl-methyl]-2-pyrrolecarboxylic acid (compound 12).

EXAMPLE 6

5-n-Propyl-3-isopropyl-1-[2'-(1H-tetrazol-5-yl)biphenyl-4-yl-methyl]-2-pyrrolecarbinol (compound 13)

Scheme 2 (Step 8)

400 mg of compound 2 (1.07 mmol) are dissolved in 10 mL of MeOH and 404 mg $NaBH_4$ (10.7 mmol) are added. The mixture is heated to reflux for 2 h, the solvent is evaporated, the mixture is adjusted to pH 6 with 2N citric acid, extracted with ethyl acetate, the combined organic phases are washed with water, dried with $Na_2SO_4$ and evaporated. Product: 250 mg. $C_{22}H_{23}N_5O$ (m.w. 373.46). Yield 63%.

EXAMPLE 7

Step 8. 2-Methyl-5-n-propyl-3-isopropyl-1-[2'-(1H-tetrazol-5-yl)biphenyl-4-yl-methyl]pyrrole (compound 15)

Scheme 2 (Step 8)

Under a nitrogen atmosphere, 0.27 g of $LiAlH_4$ (7.2 mmol) are suspended in 100 mL of anhydrous THF. 1 g of (5) (2.4 mmol) is added and the mixture is left to stand at ambient temperature for 24 h. $LiAlH_4$ is hydrolysed with water and 30% NaOH and the phases are separated. The aqueous phase is extracted repeatedly with diethyl ether, the combined organic phases are washed with water, dried with $Na_2SO_4$ and evaporated. Product: 800 mg. $C_{25}H_{29}N_5$ (m.w. 399.54). Yield 83%.

EXAMPLE 8

Scheme 4

Step 1. 4'-Aminomethyl-2-(1H-tetrazol-5-yl)biphenyl (4a)

10 g of 4'-bromomethyl-2-(1-triphenylmethyltetrazol-5-yl)biphenyl (0.018 moles), 2.03 g of trifluoroacetamide (0.018 moles), 2.4 g of potassium tert.-butylate (0.022 moles), 0.5 g of 18-crown-6 (1.8 mmol) are mixed in 80 mL of 1:1 THF/diethyl ether and left to stand at ambient temperature for 96 h. The solid is filtered out, the solvent is evaporated, the residue is redissolved with ethyl acetate and washed with 1N HCl, $NaHCO_3$, water, dried with $Na_2SO_4$ and evaporated. 9.6 g of product are obtained, which are used in the subsequent step without further purification. Formula: $C_{35}H_{26}F_3N_5O$ (m.w. 589.62). Yield 90%. The amide obtained, 9.6 g (0.016 moles), is dissolved in 50 mL of THF and 9.4 mL of 20% aqueous KOH are added. The mixture is heated to 55° C. for 5 h and is acidified with 4N HCl and left to stand overnight at ambient temperature. The solvent is evaporated, the mixture is adjusted to pH 5-6 with 30% NaOH, is filtered and washed with a little water, and is dried in a vacuum oven at 50° C. 2.8 g of product are obtained, which are used in the subsequent step without further purification. Formula: $C_{14}H_{14}ClN_5$ (m.w. 287.75). Yield 60%.

Step 2. 2,5-Dimethyl-1-[2'-(1H-tetrazol-5-yl)biphenyl-4-yl-methyl]pyrrole (compound 14)

2.8 g of (4a) (9.7 mmol), 1.1 g of acetonylacetone (9.7 mmol) and 0.5 mL of glacial AcOH in 50 mL of absolute ethanol are mixed under a nitrogen atmosphere. The mixture is heated to reflux for 6 h, the solvent is evaporated, the residue is redissolved with chloroform and water, the organic phase is washed with water, dried with $Na_2SO_4$ and evaporated. Product: 1.7 g. Formula: $C_{20}H_{19}N_5$ (m.w. 329.41). Yield 54%.

Table 1 below shows some of the compounds obtained in this manner with some physico-chemical properties which identify them, without this in any way limiting the spirit and scope of the present invention.

TABLE 1

Compounds of the formula (I)

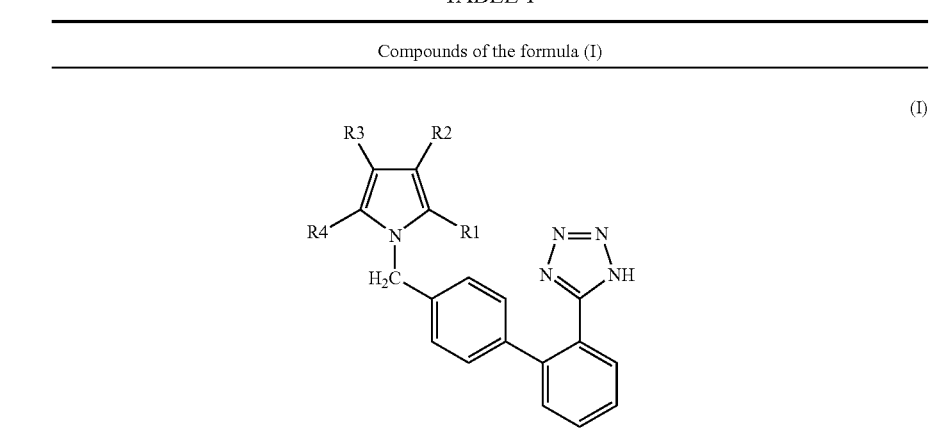

(I)

| Comp. | $R_1$ | $R_2$ | $R_3$ | $R_4$ | Formula | TLC ($R_f$) | m.p. (° C.) | $^1HNMR^{d,e}$ |
|---|---|---|---|---|---|---|---|---|
| 1 | CHO | isobutyl | H | butyl | $C_{27}H_{31}N_5O$ | $0.35^a$ | 148 | 0.8 (t, 3H); 0.9 (d, 6H); 1.3 (m, 2H); 1.5 (m, 2H); 1.8 (sept, 1H); 2.4 (t, 2H); 2.6 (d, 2H); 6.0 (s, 1H); 9.6 (s, 1H) |

TABLE 1-continued

Compounds of the formula (I)

(I)

*Structure: N-substituted pyrrole with R3, R2 at 3,4-positions, R4 and R1 at 2,5-positions, and N-CH2-biphenyl-tetrazole substituent*

| Comp. | R₁ | R₂ | R₃ | R₄ | Formula | TLC (R_f) | m.p. (°C.) | ¹HNMR[d,e] |
|---|---|---|---|---|---|---|---|---|
| 2 | CHO | H | H | propyl | $C_{22}H_{21}N_5O$ | 0.50[b] | 104 | 0.8 (t, 3H); 1.5 (m, 2H); 2.4 (t, 2H); 6.2 (d, 1H); 7.2 (d, 1H); 9.6 (s, 1H) |
| 3 | CHO | H | Br | propyl | $C_{22}H_{20}BrN_5O$ | 0.65[c] | 167 | 0.8 (t, 3H); 1.3 (m, 2H); 2.6 (t, 2H); 7.3 (s, 1H); 9.4 (s, 1H) |
| 4 | CHO | H | Cl | propyl | $C_{22}H_{20}ClN_5O$ | 0.65[c] | 150 | 0.8 (t, 3H); 1.3 (m, 2H); 2.6 (t, 2H); 7.2 (s, 1H); 9.4 (s, 1H) |
| 5 | CHO | isopropyl | H | propyl | $C_{25}H_{27}N_5O$ | 0.50[a] | 180 | 0.8 (t, 3H); 1.2 (d, 6H); 1.4 (m, 2H); 2.3 (t, 2H); 3.2 (sept, 1H); 6.1 (s, 1H); 9.6 (s, 1H) |
| 6 | CHO | isopropyl | H | butyl | $C_{26}H_{29}N_5O$ | 0.50[a] | 174 | 0.8 (t, 3H); 1.2 (d, 6H); 1.4 (m, 4H); 2.4 (t, 2H); 3.3 (sept, 1H); 6.1 (s, 1H); 9.6 (s, 1H) |
| 7 | CHO | H | H | butyl | $C_{23}H_{23}N_5O$ | 0.50[b] | 129 | 0.8 (t, 3H); 1.2 (m, 4H); 2.4 (t, 2H); 6.2 (d, 1H); 6.9 (d, 1H); 9.3 (s, 1H) |
| 8 | CHO | isopropyl | H | pentyl | $C_{27}H_{31}N_5O$ | 0.50[a] | 144 | 0.8 (t, 3H); 1.2 (m, 10H); 1.5 (t, 2H); 2.4 (t, 2H); 3.4 (sept, 1H); 6.1 (s, 1H); 9.6 (s, 1H) |
| 9 | CHO | isopropyl | H | isopentyl | $C_{27}H_{31}N_5O$ | 0.25[a] | 144 | 0.8 (d, 6H); 1.2 (d, 6H); 1.3 (m, 2H); 1.4 (sept, 1H); 2.4 (t, 2H); 3.2 (sept, 1H); 6.1 (s, 1H); 9.6 (s, 1H) |
| 10 | COOH | H | H | propyl | $C_{22}H_{21}N_5O_2$ | 0.22[a] | 134 | 0.6 (t, 3H); 1.5 (m, 2H); 2.4 (t, 2H); 6.2 (d, 1H); 7.2 (d, 1H); 11.0 (bs, 1H) |
| 11 | COOH | isopropyl | H | propyl | $C_{25}H_{27}N_5O_2$ | 0.40[a] | 170 | 0.6 (t, 3H); 0.9 (d, 6H); 1.4 (m, 2H); 2.3 (t, 2H); 3.2 (sept, 1H); 6.5 (s, 1H); 11.0 (bs, 1H) |
| 12 | COOH | H | H | butyl | $C_{23}H_{23}N_5O_2$ | 0.26[a] | 142 | 0.6 (t, 3H); 1.2 (m, 4H); 2.4 (t, 2H); 6.2 (d, 1H); 6.9 (d, 1H); 11.0 (bs, 1H) |
| 13 | CH₂OH | H | H | propyl | $C_{23}H_{23}N_5O$ | 0.20[b] | —[f] | |

TABLE 1-continued

Compounds of the formula (I)

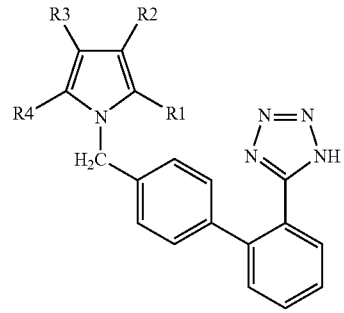

(I)

| Comp. | R₁ | R₂ | R₃ | R₄ | Formula | TLC (R$_f$) | m.p. (° C.) | ¹HNMR[d, e] |
|---|---|---|---|---|---|---|---|---|
| 14 | CH₃ | H | H | methyl | C₂₀H₁₉N₅ | 0.60[b] | 107 | 2.0 (s, 6H); 5.7 (s, 2H) |
| 15 | CH₃ | isopropyl | H | propyl | C₂₅H₂₉N₅ | 0.60[a] | 160 | 0.9 (t, 3H); 1.1 (d, 6H); 1.4 (m, 2H); 2.0 (s, 3H); 2.4 (t, 2H); 3.3 (sept, 1H); 6.1 (s, 1H) |
| 16 | CHO | 2,2-dimethylpropyl | H | butyl | C₂₈H₃₃N₅O | 0.35[a] | 136 | 0.8 (t, 3H); 0.9 (s, 9H); 1.3 (m, 2H); 1.4 (m, 2H); 2.5 (t, 2H); 2.6 (s, 2H); 6.0 (s, 1H); 9.5 (s, 1H) |
| 17 | CHO | 3-methylbutyl | H | butyl | C₂₈H₃₃N₅O | 0.35[a] | 134 | 0.8 (t, 3H); 0.9 (d, 6H); 1.3 (m, 2H); 1.5 (m, 5H); 2.4 (t, 2H); 2.7 (t, 2H); 6.0 (s, 1H); 9.6 (s, 1H) |

Notes:
[a] 9:1 CHCl₃/MeOH;
[b] 9:1 ethyl acetate/MeOH;
[c] 5:2:1 i-AmOH/acetone/water;
[d] DMSO-d₆;
[e] The signals for the benzyl methylene and biphenyl aromatics may be deemed to be identical in all the compounds: ppm 5.6 (s, 2H); 6.8 (d, 2H); 7.0 (d, 2H); 7.6 (m, 4H);
[f] amorphous solid.

Description of Pharmacological Activity

Antagonist activity at the AT₁ receptor on the part of compounds provided by the invention was assessed as the capacity to inhibit binding of the specific AII agonist to rat liver membranes. The method described by R. S. L. Chang et al., [JPET (1992), 262, 133-38] and M. J. Robertson et al., [Br. J. Pharmacol. (1992), 107, 1173-1180] was used with slight modifications. The concentration of radioligand [¹²⁹I]-Sar₁, Ile⁸-angiotensin II used was 25 pM with a membrane content corresponding to a protein concentration of approx. 25 μg of protein per sample; the incubation time was 180 minutes at 25° C. Separation of the bound from the free was carried out by rapid filtration on GFB Millipore glass fibre filters. Non-specific binding was measured in the presence of 1 μM AII which amounted to approx. 5-10% of total binding. The results obtained in this manner are shown in Table 2 which indicates, for some compounds provided by the invention and already stated by way of example in Table 1, the IC₅₀, i.e. the (nanomolar) concentration of antagonist capable of displacing 50% of the [¹²⁵I]-Sar¹, Ile⁸-angiotensin II ligand from the AT₁ receptor.

TABLE 2

Inhibition of [¹²⁵I]Sar¹, Ile⁸-angiotensin II binding in rat liver membranes (AT₁ receptor subtype)

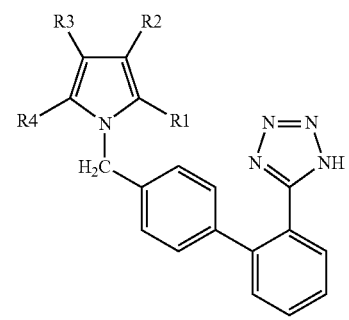

(I)

| Compounds | R₁ | R₂ | R₃ | R₄ | IC₅₀ (nm) |
|---|---|---|---|---|---|
| 1 | CHO | isobutyl | H | butyl | 8.9 |
| 2 | CHO | H | H | propyl | 72.5 |
| 3 | CHO | H | Br | propyl | 1050 |
| 4 | CHO | H | Cl | propyl | 615 |
| 5 | CHO | isopropyl | H | propyl | 35.7 |
| 6 | CHO | isopropyl | H | butyl | 15.3 |
| 7 | CHO | H | H | butyl | 66.5 |
| 8 | CHO | isopropyl | H | pentyl | 105.3 |
| 9 | CHO | isopropyl | H | isopentyl | 37.2 |
| 10 | COOH | H | H | propyl | 475 |

TABLE 2-continued

Inhibition of [$^{125}$I]Sar$^1$, Ile$^8$-angiotensin II binding in rat liver membranes (AT$_1$ receptor subtype)

(I)

| Compounds | R$_1$ | R$_2$ | R$_3$ | R$_4$ | IC$_{50}$ (nm) |
|---|---|---|---|---|---|
| 11 | COOH | isopropyl | H | propyl | 106 |
| 12 | COOH | H | H | butyl | 268 |
| 13 | CH$_2$OH | H | H | propyl | 444 |
| 14 | methyl | H | H | methyl | 10650 |
| 15 | methyl | isopropyl | H | propyl | 1193 |
| Losartan | — | — | — | — | 7.7 |
| Valsartan | — | — | — | — | 3.4 |
| Eprosartan | — | — | — | — | 1.8 |

It is clear from the data shown Table 2 that some of the compounds provided by the invention are potent AII receptor antagonists. The most potent compound of the series, compound 1, is indeed only slightly less potent than the preselected reference compounds, i.e. some AII antagonist compounds which are already used therapeutically.

It is also interesting to note that compound 1 is approx. 200 times more potent than the BPT-pyrrole derivative stated by way of example in the cited patent, EP-0323841 (8.9 nM of compound 1 vs. 1.6 µM of compound 277 of EP 0 323 841, table 5, page 81); in fact, in order to obtain truly potent compounds (i.e. with at least submicromolar activity) in this pyrrole series, it was necessary to introduce into R$_2$ an alkyl group with specific steric bulk features, such as for example the isobutyl group in compound 1 or the isopropyl group in compound 6 and a C$_3$-C$_5$ alkyl in R$_4$ instead of just methyl.

In order better to assess the therapeutic potential of the compounds provided by the invention, some of the compounds which, in vitro, proved to be the most potent in inhibiting AII binding, such as compounds 1 and 6 were subjected to in vivo assessment either in the spontaneously hypertensive rat (SHR) having an average basal arterial pressure of no less than 180 mm Hg or in the renally hypertensive rat (RHR), an animal in which partial occlusion of the renal artery brings about a progressive increase in arterial pressure which stabilises at around 200 mm Hg 3-4 weeks after surgery.

The comparison drugs used were some of the most widely therapeutically used compounds from this class such as losartan, valsartan and eprosartan. The compounds were administered intraperitoneally (I.P.) dissolved in a physiological solution as sodium salts in a volume of 5 mL/kg using various doses in the range from 5-20 mg/kg so as to be able to calculate an ED$_{15}$, i.e. the dose in mg/kg which brings about a 15% reduction in average basal systolic pressure within a period of 0-120 minutes of administration.

The values obtained in this manner are shown in Table 3, which, for each product under examination, also indicates the maximum effect produced on pressure by the dose of 15 mg/kg in the time interval under consideration.

Table 3: Reduction in systolic arterial pressure in the SHR and RHR rat brought about by (I.P.) administration of the stated compounds provided by the invention in comparison with some AII antagonists in therapeutic use.

| | SHR rat | | RHR rat | |
|---|---|---|---|---|
| | | Max. effect | | Max. effect |
| Compounds | ED$_{15}$ (mg/kg) (0-120 min) | at 15 mg/kg (% reduction vs. basal) | ED$_{15}$ (mg/kg) (0-120 min) | at 15 mg/kg (% reduction vs. basal) |
| 1 | 17.4 | 16.0 | 12.6 | 22.1 |
| 6 | 19.3 | 13.2 | 16.0 | 18.7 |
| Losartan | 25.4 | 12.0 | 16.4 | 18.9 |
| Valsartan | 26.2 | 14.4 | 16.0 | 19.0 |
| Eprosartan | NC* | 5.0 | NC* | 9.2 |

*not calculable: effect < 10% at all doses.

It is clear from the data shown in the table that the compounds provided by the invention subjected to in vivo testing exhibit a potent antihypertensive action in both SHR and RHR rats.

For example, compound 1 proved to be more active over all the parameters taken into consideration than the reference compounds losartan and valsartan, while, over the dosage range under consideration, eprosartan exhibited only slight in vivo activity despite being more active in vitro. The chemical structure of the compounds provided by the invention imparts thereto a significant and advantageous feature, namely an elevated level of absorption and metabolic stability. This is confirmed by the in vitro bioavailability data which were obtained by studying the permeability of compounds 1 and 6 provided by the invention relative to valsartan and eprosartan on monolayers of TC-7 cells, a subclone of the Caco-2 cell line [M. C. Gres et al. Pharm.; Res. 15 (1998), pages 726-733].

A→B permeability was thus assessed, namely the apparent permeability coefficient (Papp), of the compounds under investigation, tested at a concentration of 50 µM with an incubation time of 60 minutes, in the apical-to-basolateral direction. B→A permeability is reversely assessed, i.e. in a basolateral-to-apical direction, with an incubation time of 40 minutes. The results obtained are shown in Table 4 below.

TABLE 4

Average permeability (10$^{-6}$ cm/s) in TC7 cell monolayer

| Compounds | Permeability A –> B (1) | Permeability B –> A (2) | Ratio (1/2) |
|---|---|---|---|
| Compound 1 | 27.9 | 3.4 | 8.2 |
| Compound 6 | 15.4 | 1.0 | 15.4 |
| Valsartan | 0.2 | 0.2 | 1.0 |
| Eprosartan | 0.1 | 0.4 | 0.25 |

It is clear from the data shown in the table that, for the investigated compounds provided by the invention, transcellular transport is much greater in the direction of absorption, i.e. with apical to basolateral flow (A→B) relative to flow in the reverse direction (B→A). In contrast, both valsartan and eprosartan exhibit little ability to flow through a TC7 cell monolayer, which is a cell line derived from the human intestinal epithelium. This difference in bioavailability is important because it can explain how, for example, compound 1 proved to be the most active of all the AII antagonist compounds subjected to "in vivo" testing, while being respectively approx. ⅗ times less potent than valsartan and eprosartan "in vitro".

The invention claimed is:

1. A compound represented by a general formula (I) shown below and in which:

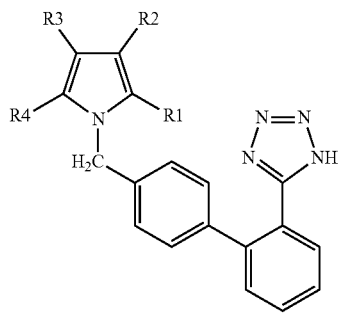

(I)

R1 is
—CHO,
R2 is a linear or branched C3-C4 alkyl group
R3 is hydrogen
R4 is a linear or branched C3-C5 alkyl group
and the pharmaceutically acceptable salts thereof.

2. The compound according to claim 1, in which R4 is an n-butyl group and the pharmaceutically acceptable salts thereof.

3. A pharmaceutical preparation comprising as active substance the compound according to claim 1 or a pharmaceutically acceptable salt thereof.

4. A pharmaceutical preparation according to claim 3 wherein said compound is present in an amount to provide a dosage of from 0.125 to 5 mg/kg to a patient for the treatment of arterial hypertension and congestive cardiac insufficiency.

5. A pharmaceutical preparation according to claim 3 further comprising inactive pharmaceutically acceptable ingredients selected from the group consisting of carriers, binders, flavourings, sweeteners, disintegrants, preservatives, humectants and mixtures thereof, or ingredients which facilitate transdermal or transmucosal absorption or which permit controlled release of the active substance over time, together with those ingredients suitable for parenteral use.

6. The compound according to claim 1, wherein said pharmaceutically acceptable salts are selected from the group consisting of a sodium or potassium salt.

* * * * *